United States Patent [19]

Hytonen

[11] 3,998,225
[45] Dec. 21, 1976

[54] DEVICE FOR TAMPONS

[75] Inventor: Valjo Nikodemus Hytonen, Helsinki, Finland

[73] Assignee: Salve S. A., Geneva, Switzerland

[22] Filed: May 14, 1975

[21] Appl. No.: 577,406

[30] Foreign Application Priority Data

May 29, 1974 Sweden ............................ 7407073

[52] U.S. Cl. .............................. 128/263; 128/270
[51] Int. Cl.² .................. A61F 16/00; A61F 13/20
[58] Field of Search .......... 128/270, 262, 263, 285

[56] References Cited
UNITED STATES PATENTS

| | | | |
|---|---|---|---|
| 2,268,536 | 12/1941 | Seidler | 128/262 |
| 2,355,917 | 8/1944 | Knight | 128/263 |
| 3,058,469 | 10/1962 | Crockford | 128/285 |
| 3,204,635 | 9/1965 | Voss et al. | 128/263 |
| 3,358,686 | 12/1967 | Asaka | 128/263 |

Primary Examiner—Aldrich F. Medbery

[57] ABSTRACT

A device in the form of a sleeve for facilitating the insertion of a tampon into the vagina. The string of the tampon is received in a slit at one end of the sleeve, said slit defining a cylindrical portion which functions as a support for the tampon when the tampon has been partially moved out of the sleeve.

2 Claims, 2 Drawing Figures

DEVICE FOR TAMPONS

BACKGROUND OF THE INVENTION

The present invention relates to a device for facilitating the insertion of a tampon into the vagina, said tampon being provided with a string in the usual manner.

The object of the present invention is to provide a device for said purpose which is simpler in construction, takes less space, is cheaper to manufacture and is easier to use in inserting the tampon than previously known aids for inserting a tampon into the vagina.

The device of the invention is characterised in that it consists of a single cylindrical body, i.e. made in one piece, in which the tampon is normally stored. The body is provided at one end thereof with a notch or slit to receive the string of the tampon; the free end of the string being located outside the body, while the string end of the tampon in its storage position faces away from the end of the body which is provided with the notch or slit. The notch or slit defines a portion of the cylindrical body which acts as support for retention of the tampon in the body after the tampon has been moved partially out of the body by pulling the tampon string a distance corresponding to the distance between the string end of the tampon and the bottom of the notch in the storage position of the tampon. The tampon is held or secured in this protruding initial position for insertion into the vagina, by holding or clamping the string of the tampon against the end portion of the body facing away from the end provided with the notch or slit, at the same time as the tampon is supported by the support or retaining portion.

BRIEF DESCRIPTION OF THE DRAWINGS

The invention will be further described with reference to the drawing wherein.

DESCRIPTION OF THE INVENTION

Figure 1:
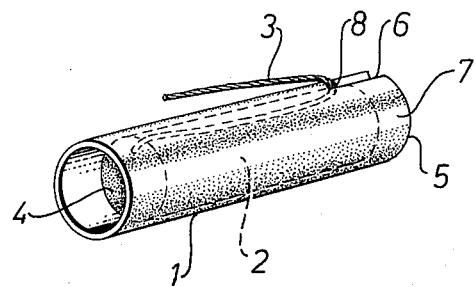
FIG. 1 shows an embodiment of the novel device with a tampon inserted therein.

The device consists of a single tubular body or sleeve 1 which, in the embodiment shown consists of a cylinder open at both ends. The sleeve-formed or cylindrical body 1 contains or receives a tampon 2 which in known manner is provided with a draw-string 3 attached to or within the tampon and protruding from one end of the tampon which is, in the following referred to as the string end 4. At one end 5 the cylindrical body 1 is provided with a slit or notch 6 which, in the embodiment shown, extends in the longitudinal direction of the body 1, but which may also extend at an angle to this longitudinal direction if desired. The notch is preferably open at the end 5 so that the string 3 can be easily inserted in the notch. The notch 6 is designed to received the tampon string 3 as shown in the drawing, the free end of the string being located outside the body. The tampon is inserted into the cylindrical body 1 through the notch end 5 so that the string end 4 of the tampon faces away from the notch end 5 of the cylindrical body 1, as shown in FIG. 1.

Figure 2:
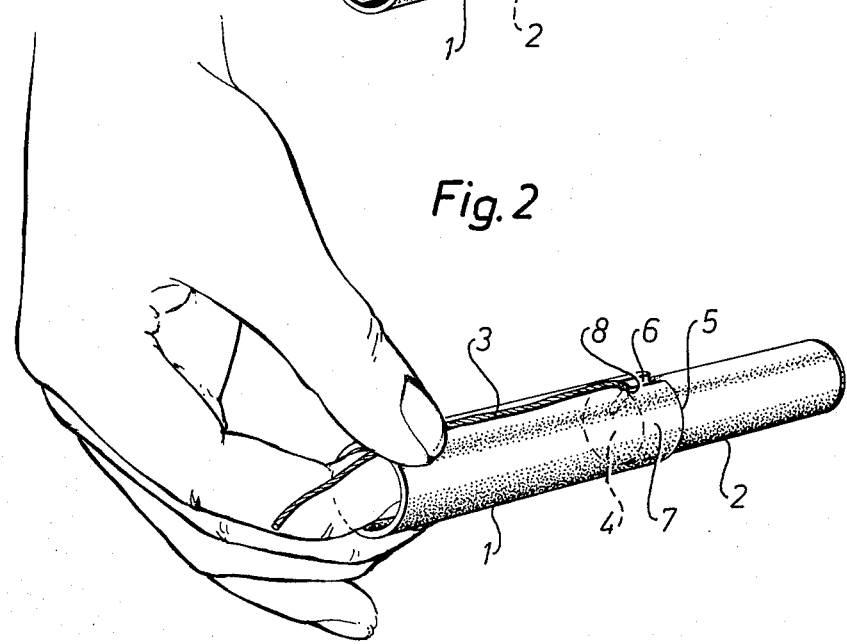
FIG. 2 illustrates the use of the device of FIG. 1 in connection with insertion of the tampon into the vagina.

The length of the notch 6 determines the length of a portion of the cylindrical body 1 which serves as support or retaining portion 7 for the tampon after this has been moved out to the position shown in FIG. 2 preparatory to inserting the tampon into the vagina. When the string 3 is pulled gently it will slide or run in the notch 6 of the cylindrical body so that the tampon will be moved from its storage position shown in FIG. 1 to the initial position shown in FIG. 2 ready for insertion of the tampon into the vagina. This movement of the tampon by means of the string 3 is thus completed when the string end 4 of the tampon reaches the bottom edge 8 of the notch 6. The tampon is thus moved out of the body a distance corresponding to the distance between the string end 4 of the tampon and the bottom edge 8 of the notch seen when the tampon is in its storage position. When the tampon has been fully pulled out by means of the string 3, the string is gently stretched by the fingers and held or secured thus stretched by inserting the forefinger into the cylindrical body 1 and pressing the thumb against the outer surface of the cylindrical body 1 so that the stretched string is held securely between thumb and body 1 as shown in FIG. 2. This stretching and retention of the string secures the tampon in its initial position ready for insertion into the vagina since a portion of the tampon, determined by the length of the notch 6, remains in the support or retaining portion 7 of the cylindrical body, which thus acts as support and guide for the tampon so that the centre line of the tampon will coincide or substantially coincide with the centre line of the cylindrical body. When the tampon has been inserted into the vagina with the help of this cylindrical body, the string is released and the cylindrical body withdrawn, the tampon thus being released from the cylindrical body and remaining in the position inserted.

The inner diameter of the cylindrical body 1 is determined so that the tampon slides easily inside the body and is easily released from the support or retaining portion 7 after insertion of the tampon into the vagina without the position of the tampon being altered or objectionably altered when the cylindrical body is withdrawn. However, the inner diameter of the body should not be so great that the tampon is inclined to any great extent in relation to the cylindrical body when the tampon assumes its initial position fixed by the string 3 for insertion into the vagina, which might prevent the necessary guidance and retention of the tampon laterally due to too great clearance between tampon and support or retaining portion 7. On the other hand, if the inner diameter of the cylindrical body is too small, this might result in the tampon, which is somewhat compressible, not being easily released from the body when the body is withdrawn after insertion of the tampon into the vagina. It is therefore preferred that the inner diameter of the body 1 substantially corresponds to the diameter of the tampon.

The length of the notch 6 is determined depending on how large a support or retaining portion 7 is considered necessary to achieve suitable guidance and support of the tampon and to enable the tampon to be released from the support or retaining portion 7 in the vagina at a specific inner diameter of the body or support or retaining portion. The length of the notch 6 is preferably about 7 to 13 mm, but shorter or longer notches may be used, if desired. The bottom edge 8 of the notch 6 is preferably rounded to prevent damage to the tampon string during pulling and so that the string slides easily in the notch without pinching. The bottom edge 8 may be reinforced in a suitable manner, if desired.

The sleeve-formed body, which may consist of any suitable material such as cardboard, paper or plastics materials, has substantially the same length as the tampon or longer than this. Since the sleeve-formed body also functions to protect the tampon 2 during storage, the body should not be shorter or substantially shorter than the tampon. The tampon and cylindrical body are preferably enclosed in a sealed casing or envelope of paper or other suitable material.

What is claimed is:

1. A device for facilitating the insertion of a tampon into the vagina, said tampon having a string attached at one end thereto, said device comprising a sleeve-like body in which the tampon is normally stored, said sleeve being provided at one end with a means for moving said tampon out of said body comprising a notch opening outwardly at the end of said body to receive said string, with the free end of the string located outside the body and the string end of the tampon in the storage position within said body facing away from said notch, said notch defining a portion of the body which acts as support or restraint for the tampon after the tampon has been partially moved out of the body by pulling said tampon strong a distance corresponding to the distance between said string end of the tampon and the bottom edge of the notch, so that the tampon is held or secured in this protruding position for insertion into the vagina.

2. The device according to claim 1, wherein the notch extends substantially in the longitudinal direction of the cylindrical body.

* * * * *